United States Patent
Planard-Luong

(10) Patent No.: US 11,090,487 B2
(45) Date of Patent: Aug. 17, 2021

(54) DEVICE FOR TREATING HUMAN KERATIN MATERIALS, IN PARTICULAR WITH THE AID OF AN ELECTRIC CURRENT

(71) Applicants: L'OREAL, Paris (FR); SEB S.A., Ecully (FR)

(72) Inventor: Thi Hong Lien Planard-Luong, Chevilly la Rue (FR)

(73) Assignees: L'OREAL, Paris (FR); SEB S.A., Ecully (FR)

( * ) Notice: Subject to any disclaimer, the term of this patent is extended or adjusted under 35 U.S.C. 154(b) by 115 days.

(21) Appl. No.: 16/062,913

(22) PCT Filed: Dec. 6, 2016

(86) PCT No.: PCT/EP2016/079927
§ 371 (c)(1),
(2) Date: Jun. 15, 2018

(87) PCT Pub. No.: WO2017/102454
PCT Pub. Date: Jun. 22, 2017

(65) Prior Publication Data
US 2019/0001125 A1    Jan. 3, 2019

(30) Foreign Application Priority Data
Dec. 17, 2015    (FR) ...................... 1562639

(51) Int. Cl.
*A61N 1/32*    (2006.01)
*A61N 1/04*    (2006.01)
(Continued)

(52) U.S. Cl.
CPC ........... *A61N 1/325* (2013.01); *A61N 1/0444* (2013.01); *A61N 1/0448* (2013.01); *A61N 1/26* (2013.01); *A61N 1/303* (2013.01); *A61N 1/328* (2013.01)

(58) Field of Classification Search
CPC .... A61N 1/325; A61N 1/0444; A61N 1/0448; A61N 1/26; A61N 1/303; A61N 1/328
(Continued)

(56) References Cited

U.S. PATENT DOCUMENTS

| 4,858,600 A | 8/1989 | Gross et al. |
| 5,090,402 A | 2/1992 | Bazin et al. |

(Continued)

FOREIGN PATENT DOCUMENTS

| CN | 1313213 C | 5/2007 |
| CN | 101020513 A | 8/2007 |

(Continued)

OTHER PUBLICATIONS

Non-Final Office Action in U.S. Appl. No. 16/062,183 dated Feb. 20, 2020.
(Continued)

*Primary Examiner* — Phillip A Gray
(74) *Attorney, Agent, or Firm* — Shumaker, Loop & Kendrick, LLP

(57) ABSTRACT

A device for treating human keratin materials, in particular with the aid of an electric current. The device includes a reservoir containing an in particular cosmetic or dermatological composition to be applied to the keratin materials, a unit for dispensing the composition contained in the reservoir, in particular a pump, and an end fitting for applying the composition contained in the reservoir, comprising at least one applying member and in particular a plurality of applying members. The applying member is supplied with the composition from the reservoir by the dispensing unit, the composition passing through an intermediate chamber for storing the composition located in the end fitting, the intermediate chamber being at least partially defined by an elastically deformable wall.

13 Claims, 3 Drawing Sheets

(51) Int. Cl.
  *A61N 1/26* (2006.01)
  *A61N 1/30* (2006.01)
(58) Field of Classification Search
  USPC .......................................................... 604/20
  See application file for complete search history.

(56) References Cited

U.S. PATENT DOCUMENTS

| | | | |
|---|---|---|---|
| 5,131,384 | A | 7/1992 | Obagi |
| 6,535,761 | B2 | 3/2003 | Bernabei |
| 6,947,791 | B2 | 9/2005 | Zhang et al. |
| 7,775,735 | B2 | 8/2010 | Habatjou |
| 2005/0107832 | A1 | 5/2005 | Bernabei |
| 2005/0209538 | A1 | 9/2005 | Lev et al. |
| 2006/0076361 | A1* | 4/2006 | Rueschhoff ........... B29B 7/7438 222/94 |
| 2008/0200861 | A1 | 8/2008 | Shalev et al. |
| 2010/0217176 | A1 | 8/2010 | Carrara et al. |
| 2010/0274329 | A1 | 10/2010 | Bradley et al. |
| 2012/0109041 | A1 | 5/2012 | Munz |
| 2012/0121309 | A1 | 5/2012 | Liu |
| 2013/0204178 | A1 | 8/2013 | Luzon et al. |
| 2013/0264358 | A1 | 10/2013 | Fallat, II et al. |
| 2015/0190074 | A1 | 7/2015 | McRae |

FOREIGN PATENT DOCUMENTS

| | | |
|---|---|---|
| CN | 101532190 A | 9/2009 |
| CN | 203777287 U | 8/2014 |
| CN | 103249339 A | 2/2017 |
| EP | 1885217 A2 | 2/2008 |
| FR | 2619308 A1 | 2/1989 |
| FR | 2917299 A1 | 12/2008 |
| FR | 3015300 A1 | 6/2015 |
| GB | 2372705 A | 9/2002 |
| JP | S48108873 U | 12/1973 |
| JP | H01135015 U | 9/1989 |
| JP | H0271742 A | 3/1990 |
| JP | 2002369985 A | 12/2002 |
| JP | 2009-179915 A1 | 8/2009 |
| JP | 2011502656 A | 1/2011 |
| JP | 2013544282 A | 12/2013 |
| JP | 2015510419 A | 4/2015 |
| RU | 2270041 C2 | 2/2006 |
| RU | 2010123941 A | 12/2011 |
| WO | 2006130643 A2 | 5/2006 |
| WO | 2008/057640 A2 | 5/2008 |
| WO | 2010111997 A2 | 10/2010 |
| WO | 2013118114 A1 | 8/2013 |
| WO | 2014/180555 A1 | 11/2014 |
| WO | 2014180555 A1 | 11/2014 |
| WO | 2014/207750 A1 | 12/2014 |
| WO | 2015/091044 A1 | 6/2015 |
| WO | 2015091044 A1 | 6/2015 |
| WO | 2015097624 A1 | 7/2015 |

OTHER PUBLICATIONS

Non-Final Office Action in U.S. Appl. No. 16/062,209 dated Feb. 20, 2020.
International Search Report dated Mar. 21, 2017 in International Patent Application No. PCT/EP2016/079911 (3 pages).
Written Opinion dated Mar. 21, 2017 in International Patent Application No. PCT/EP2016/079911 (5 pages).
International Preliminary Report on Patentability dated Jun. 19, 2018 in International Patent Application No. PCT/EP2016/079911 (6 pages).
International Search Report dated Mar. 21, 2017 in International Patent Application No. PCT/EP2016/079915 (3 pages).
Written Opinion dated Mar. 21, 2017 in International Patent Application No. PCT/EP2016/079915 (5 pages).
International Preliminary Report on Patentability dated Jun. 19, 2018 in International Patent Application No. PCT/EP2016/079915 (6 pages).
International Search Report dated Mar. 21, 2017 in International Patent Application No. PCT/EP2016/079923 (3 pages).
Written Opinion dated Mar. 21, 2017 in International Patent Application No. PCT/EP2016/079923 (5 pages).
International Preliminary Report on Patentability dated Jun. 19, 2018 in International Patent Application No. PCT/EP2016/079923 (6 pages).
International Search Report dated Feb. 24, 2017 in International Patent Application No. PCT/EP2016/079927 (3 pages).
Written Opinion dated Feb. 24, 2017 in International Patent Application No. PCT/EP2016/079927 (5 pages).
International Preliminary Report on Patentability dated Jun. 19, 2018 in International Patent Application No. PCT/EP2016/079927 (6 pages).
International Search Report dated Mar. 24, 2017 in International Patent Application No. PCT/EP2016/079922 (3 pages).
Written Opinion International Search Report dated Mar. 24, 2017 in International Patent Application No. PCT/EP2016/079922 (5 pages).
International Preliminary Report on Patentability dated Jun. 19, 2018 in International Patent Application No. PCT/EP2016/079922 (6 pages).
Russian Office Action of Substantive Examination for RU Application No. 2018121748/14 (034416) dated Apr. 2, 2019 with English Translation (10 pages).
Russian Office Action of Substantive Examination for RU Application No. 2018121755/14 (034427) dated Apr. 2, 2019 with English Translation (10 pages).
Russian Office Action of Substantive Examination for RU Application No. 2018121754/14 (034423) dated Apr. 2, 2019 with English Translation (8 pages).
Russian Office Action of substantive examination for RU Application No. 2018121971/14 dated Mar. 18, 2019; 13 pages (includes English Translation).
Japanese Office Action for JP2018-531659 dated Jun. 21, 2019 with English Translation (10 pages).
Japanese Office Action for JP2018-531657 dated Jul. 1, 2019 with English Translation (11 pages).
Japanese Office Action for JP2018-531653 dated Jul. 29, 2019 with English Translation (12 pages).
Japanese Office Action for JP2018-531626 dated Aug. 5, 2019 with English Translation (8 pages).
Japanese Office Action for JP2018-531627 dated Jun. 3, 2019 with English Translation (7 pages).
Non-Final Office Action in U.S. Appl. No. 16/061,875 dated Apr. 2, 2020.
First Office Action for CN Patent App. No. 201680074289.9 with English Translation dated Jul. 3, 2020 (12 pages).
Final Rejection for U.S. Appl. No. 16/062,183 dated Aug. 13, 2020 (13 pages).
Final Rejection for U.S. Appl. No. 16/062,209 dated Jun. 24, 2020 (12 pages).
Korean Office Action for Korean Pat. App. No. 10-2018-7017071 dated Jun. 20, 2020 (10 pages).
Non-Final Office Action for U.S. Appl. No. 16/062,924 dated Aug. 5, 2020 (11 pages).
Final Rejection for U.S. Appl. No. 16/061,875 dated Aug. 5, 2020 (12 pages).
Non-Final Office Action for U.S. Appl. No. 16/062,209 dated Nov. 9, 2020 (10 pages).
Advisory Action for U.S. Appl. No. 16/061,875 dated Nov. 9, 2020 (3 pages).
English Translation of First Office Action for Chinese Pat. Application No. 201680074631.5, dated Apr. 9, 2021 (6 pages).
Non-Final Office Action for U.S. Appl. No. 16/061,875, dated Jan. 6, 2021 (16 pgs.).
Non-Final Office Action for U.S. Appl. No. 16/062,209, dated May 26, 2021 (9 pages).
Corrected Notice of Allowability for U.S. Appl. No. 16/062,924, dated May 24, 2021 (7 pages).

(56) References Cited

OTHER PUBLICATIONS

Notice of Allowance for U.S. Appl. No. 16/062,924, dated Mar. 30, 2021 (10 pages).
Final Rejection for U.S. Appl. No. 16/061,875, dated Jun. 28, 2021 (16 pages).

* cited by examiner

DEVICE FOR TREATING HUMAN KERATIN MATERIALS, IN PARTICULAR WITH THE AID OF AN ELECTRIC CURRENT

BACKGROUND

The present invention relates to devices intended to treat keratin materials, in particular the skin, scalp or hair, in particular cosmetically or dermatologically. By "cosmetic or dermatological composition" what is meant is any composition such as defined in Directive 93/35/CEE of the Council of 14 Jun. 1993.

The invention relates in particular to devices, in particular cosmetic or dermatological devices, for treating keratin materials with the aid of an electric current.

It is known that the application of an electric current to the skin may facilitate the penetration of an active agent. It is thus known to treat human keratin materials using iontophoresis devices. Iontophoresis non-invasively allows active agents to diffuse through the skin by virtue of an electrical stimulation. The magnitude of the administered current or its polarity (anodic or cathodic current) may be adjustable. The transcutaneous diffusion of the molecules via the iontophoresis is based on two effects, namely electrorepulsion and electro-osmosis.

Electrorepulsion is the migration of ionized molecules caused by repulsion of charges of the same sign. Thus, a positively charged substance will diffuse through skin placed next to the anode (+).

Electro-osmosis is the migration of even unionized molecules caused by friction related to the stream of water that flows from the anode to the cathode during iontophoresis. Under the effect of a current, water or a solvent conveys, during migration, dissolved substances.

U.S. Pat. No. 5,090,402 relates to an applicator of electric current also having a massaging function, the applicator comprising a plurality of balls, all the balls being immersed in a composition reservoir that extends under a holder of the balls.

The subject of U.S. Pat. No. 5,131,384 is a massaging applicator comprising a plurality of balls, a central ball of which is supplied directly with product. This massaging applicator is devoid of a system for applying an electric current.

In patent application US 2005/0107832 the applicator comprises a matrix of electrodes.

SUMMARY

There is a need to further improve devices that promote the penetration of active agents through the skin, in order to increase iontophoresis effectiveness.

There is in particular need for a device for treating keratin materials, in particular cosmetically or dermatologically, in particular with the aid of an electric current, that is highly effective and may be used with comfort and in complete safety.

The subject of the invention is thus, according to one of its aspects, a device for treating human keratin materials, in particular cosmetically or dermatologically, with the aid of an electric current, comprising at least:
- a reservoir containing a composition P to be applied to the keratin materials, in particular a cosmetic or dermatological composition,
- a dispensing unit for dispensing the composition contained in the reservoir, in particular a pump,
- an end fitting for applying the composition contained in the reservoir, comprising at least one applying member and in particular a plurality of applying member, the applying members being supplied with composition from the reservoir by the dispensing unit, the composition passing through an intermediate chamber for storing the composition located in the end fitting, the intermediate chamber being at least partially defined by an elastically deformable wall.

The elastically deformable wall is movable under the pressure of the composition between a first position, and a second position in which the intermediate chamber for storing the composition is formed.

By "human keratin materials" what is meant is mainly the skin (in particular of the body or face) or else the scalp, the nails or the hair.

The treatment may in particular be carried out using an electric current.

The presence of the intermediate chamber allows intermediate storage of a small amount of composition, thereby possibly allowing the dispensation of the composition onto the keratin materials to be smoothed even if the dispensation thereof by the dispensing unit from the reservoir occurs in fits and starts, this possibly in particular being the case when the dispensing unit is actuated manually, for example by means of a dispensing button, or automatically, for example by means of a jerky motor. The dispensing unit may thus be configured to dispense the composition in fits and starts.

The dispensing unit may be actuated manually. As a variant, the dispensing unit is actuated automatically, for example by means of an electric motor. The electric motor need not be a stepper motor, which may be relatively expensive, thereby allowing a less expensive device to be employed.

The dispensing unit may include at least one motor, in particular at least one geared non-servo motor, a DC motor for example. Such a device may allow the motor to be powered for a given amount of time and not continuously. The dispensing unit may in particular be devoid of a grub screw and pinion, or a stepper motor, or a geared motor servo-controlled to revolution count.

The maximum volume of the intermediate chamber may be comprised between 5 and 100 microliters (μL) and better still between 10 and 50 μL or even between 15 and 40 μL, for example being about 20 μL. The elastically deformable membrane may deform to modify the volume of the intermediate chamber. This variation is necessary to absorb the fits and starts of the dispensing unit, of the pump for example.

The device may be configured to allow the composition to be dispensed onto the keratin materials with a flow rate comprised between 0.5 and 20 μL/s and better still between 1 μL/s and 10 μL/s, the flow rate for example being about 2 to 4 μL/s. The device according to the invention thus advantageously allows the composition to be dispensed with a very low flow rate, this possibly being advantageous in the case of an iontophoresis treatment.

The presence of the intermediate chamber allows the control of the flow rate output from the device to be improved, whatever the nature of the dispensing unit used. Preferably, the composition output from the device is thus dispensed continuously and not discontinuously, even if the dispensation by dispensing unit may occur in fits and starts. The regularity of the flow rate with which the composition is dispensed is important in an iontophoresis treatment because it allows the effectiveness and stability of the applied micro-current, and therefore the comfort of the user during the treatment, to be guaranteed.

The use of the device according to the invention is particularly advantageous in the case of a composition the viscosity of which varies over time as the device is used. Specifically, the presence of the intermediate chamber allows any variation in the viscosity of the composition to be compensated. The viscosity variation may result from long-term storage in the reservoir before use of the amount of composition contained in the reservoir.

A height h of the intermediate chamber extends between the first position of the applying member and its second position.

Intermediate Chamber

The elastically deformable wall of the intermediate chamber may comprise an elastically deformable membrane. The elastically deformable membrane may be disk-shaped. It may comprise a channel for conveying the composition into the intermediate chamber. This channel may allow the composition to be conducted from the reservoir to the intermediate chamber.

The end fitting may comprise a distributor bounding the intermediate chamber for storing the composition. The distributor may comprise at least one orifice for supplying the applying member with composition and in particular a plurality of supplying orifices, these conducting the composition from the intermediate chamber as far as the applying members, which are in particular between two and eight in number. The latter may for example be placed in a triangle or hexagon.

The size of the supplying orifices may be calculated so that the elastically deformable wall deforms under the pressure of the composition.

During use, the composition may remain on the one or more applying members until the composition makes contact with the keratin materials, this possibly modifying the surface tension of the composition. The surface tension of the composition may then exceed a threshold value, from which the composition may exit via the one or more orifices.

The membrane deforms no more than is necessary to overcome the surface tension of the supplying orifices.

The distributor may be configured so that the flow rate of composition reaching at least two of and better still each applying members is identical to within 20%, better still to within 15%, and even better still to within 10%. The flow rate of the composition reaching the applying members is the flow rate of the composition exiting the supplying orifice corresponding to the applying member in question, to supply the accommodation of said applying member. Two flow rates $D_1$ and $D_2$ are compared in the following way. $D_1$ being the lowest of the two and $D_2$ the highest of the two, the following ratio is calculated: $(D_2-D_1)/D_2$.

Electrically Conductive Distributor

The distributor may be electrically conductive.

The material or materials of the distributor may be chosen from the following list, which is non-limiting: acetal, polyester, ABS, polyamide, polycarbonate, PP, PE, silicone, butyl, nitrile, viton, PBT, and a combination of these materials. It may in particular be a plastic, for example preferably polycarbonate.

The material of the distributor may be made electrically conductive by inserting a filler into the polymer matrix, this filler possibly being chosen from the following list, which is non-limiting: metal, graphite or carbon powder or fibers.

In one embodiment, the distributor is formed from at least one thermoplastic, which comprises an electrically conductive filler, for example a carbon filler or a metallic filler. A carbon filler is preferred so as to ensure that the distributor is fairly lightweight.

In one embodiment, the applying members are not electrically conductive.

The distributor may be electrically connected to an electrical supply system by a metallic lug. The latter may make it possible to ensure the transfer of electric current from the electrical supply system to the distributor. The distributor and the composition may be the only components in the end fitting that are electrically conductive. In particular, the cap, the lid and/or the applying members might not be electrically conductive. The only component that makes contact with the skin and that is electrically conductive may be the composition.

Applying Member

The device comprises a plurality of applying members, in particular between two and eight and better still between three and six, in particular in the form of balls. The multiplicity of applying members continuously promotes good distribution of the composition and where appropriate improves the ionization of the composition during treatment. The multiplicity of applying members also allows the massaging effect during the treatment to be improved.

At least one applying member may be a ball, and better still all the applying members are balls.

As a variant, the applying members may have any profile and may in particular have a cylindrical profile, then for example taking the form of rollers, or a non-cylindrical profile, then for example having an ovoid or discoid shape.

At least some of the applying members may be organized in a polygon, in particular a hexagon or a triangle, and better still all the applying members are organized in a polygon, in particular as a hexagon or a triangle. Such a triangle arrangement facilitates the application and the treatment of zones that are difficult to access, the wings of the nose for example.

This configuration of the applying members also promotes good distribution of the composition over the whole of the application area. A treatment of better uniformity is thus obtained. Safety and comfort, which are associated with a good distribution of the electric current over the application area, are also improved where appropriate. The arrangement of the applying members and the relatively high number thereof allow simultaneous application over a fairly large area.

The applying members may be made of plastic or metal.

The applying members are preferably neither electrically conductive, nor linked to the electrical supply circuit by metal conductors.

The outer surface of an applying member may be totally inert from a chemical point of view with respect to the composition applied and the keratin materials. The outer surface may be covered with a varnish. The outer surface may be polished. The outer surface may where appropriate comprise a biocidal material.

The applying members may be spherical or cylindrical, roller-shaped for example, or have some other, in particular ovoid, shape.

Advantageously, at least one applying member, better still each applying member, turns about at least one rotation axis. In one exemplary implementation of the invention, the outer surface of the applying member is substantially axisymmetric about an axis of symmetry, the outer surface being able to be rotary about this axis of symmetry. As a variant, the applying member may be able to rotate about a rotation axis that is distinct from this axis of symmetry.

At least one applying member may comprise a core to which an outer wall is attached. This may be the case for all the applying members. This core may comprise a textured surface and the outer wall may be able to deform during the application so as to come into contact with the texture. The latter makes it possible to produce a massaging effect when the applying member is in contact with the surface to be treated, and this may inter alia facilitate the penetration of the composition into the skin and promote its action.

As a variant, the outer wall may be rigid.

In one exemplary implementation of the invention, the outer wall comprises a texture, which may comprise bumps or ribs.

Alternatively, at least one applying member may comprise removable elements which give the applying member a texture. It is thus possible to change these elements with a view to modifying the dimensions of the applying members, their surface properties, or even their roughness.

Advantageously, at least one applying member is removably mounted on the device. All the applying members may be removably mounted on the device.

In one variant embodiment, the applying member takes the form of an end fitting for hair, for example comprising a comb. It may in particular comprise at least one possibly hollow tooth.

The distributor may include a first face on which the applying members are positioned, which face may be planar, concave or convex. It is for example slightly domed. The distributor comprises a second face opposite the first, which face may be planar, concave or convex.

Electrical Supply System

The device may comprise an electrical supply system for exposing the keratin materials to an electrical treatment current in a zone of application of the composition.

The expression "electrical supply system" is understood to mean an electrical assembly that is able to induce a potential difference between one or more electrodes and at least one counter electrode. If the end fitting is placed on a person's face and if the counter electrode is held in one hand, the potential difference is established between the person's face and his hand.

Electrodes

The electrical supply system may include an electrode located remotely from the keratin materials and making contact with the composition, and a counter electrode, preferably making contact with the keratin materials in a zone that is not exposed to the composition.

According to the invention, what is meant by an "electrode" is a positively charged electrode (anode) or a negatively charged electrode (cathode). This electrode may be placed in the applying end fitting, so as to ensure the electric current passes through the composition. The electrode is then placed inside the end fitting. In this case, it does not make direct contact with the keratin materials, but with the composition itself. The composition may be the only conductive substance making contact with the skin during use of the device. The electrode may not make contact with the keratin materials, in particular the skin, the end fitting comprising no electrically conductive materials making contact with the skin.

Throughout the text, the term "electrode" means a single insulated electrode. An electrode may take the form of a ball, stud or tongue for example. The device may comprise one or more electrodes.

What is meant by "counter electrode" is an electrode brought to a potential above the other electrode (cathode) or below the other electrode (anode). The sign of the polarity of the counter electrode is the opposite of that of the electrode. In general, said counter electrode is placed on the body of the device or in a handpiece. The counter electrode is intended to be brought into contact with an area of the body of the person undergoing the care treatment. For example, it may be held between the person's palm and fingers. In one configuration, the counter electrode is placed in on the end fitting. In this case, it is separated from the electrode by an insulating space and kept as far as way as possible from the electrode in order to prevent any current leakage.

The electrode may be housed inside the end fitting, the electrode in particular being kept away from the outer wall of the applying member by a distance comprised between 0.2 mm and 5 mm. This distance is the separation between the electrode and the outer surface of the applying member. This distance is the shortest measurable distance between the electrode and the outer wall of the applying member. It is measured between any point on the electrode and the outer wall of the applying member, provided that the distance measured is the shortest distance.

Advantageously, the electrical supply system includes a current generator able to control the magnitude of the treatment current flowing between the electrode and skin, thereby allowing the voltage U between the electrode and the counter electrode to be controlled. The voltage U generated depends on the impedance of the "skin+composition" system. The voltage U is limited to a maximum value $U_{max}$ deliverable by the current generator, for safety reasons (about 100 V for example). This voltage $U_{max}$ may be lower than 150 V.

The electrode may be flat, for example taking the form of a flat disc or polygon. The electrode may be hollow, for example being formed by stamping or bending an electrically conductive sheet. The electrode may be porous.

Electrical Parameters

The electrical power source may comprise any cell stack or accumulator. The voltage between the electrodes is for example between 1.2 V and 24 V and preferably between 1.2 and 3.3 V. If appropriate, the passage of the current may create spot heating.

The device may in particular deliver an equivalent current density to the skin of preferably 0.500 mA/cm$^2$ or less, between 0.01 mA/cm$^2$ and 0.500 mA/cm$^2$ for example, and for example of between 0.1 mA/cm$^2$ and 0.3 mA/cm$^2$.

Controlling System and Warning Facility

The device may furthermore comprise a controlling system sensitive to the impedance of the skin. The controlling system may be configured to perform a measurement giving information on the impedance of the skin. By "measurement", what is meant is that the measured magnitude is compared with a threshold value, for example whether or not the measured magnitude has exceeded the threshold value, or whether or not the measured magnitude is located in a given interval.

The device may furthermore comprise a warning facility providing the user with a signal in response to information originating from the controlling system sensitive to the impedance of the skin. The warning facility may thus make it possible to forewarn the user that the measured impedance has exceeded a threshold value.

The delivered signal may in particular relate to the need, if there is one, to modify the current density between the electrodes and/or the amount of composition to dispensed. This modification may for example be carried out automatically by a servo-controlling system of the device, or indeed manually by the user. The signal may for example invite the user to dispense an additional composition dose. The signal may as a variant or additionally invite the user to increase the current density.

The threshold value or values of the warning facility may be preprogrammed into the device, or indeed be set by the user, or even depend on the composition reservoir introduced into the device, if the reservoir is recognized by the device and if a corresponding threshold is automatically determined depending on an identifier of the reservoir.

If there is not enough composition between the electrode and the skin, the impedance is very high. The voltage U may become too high.

If the quantity of composition between the electrode and the skin increases, the voltage U may decrease on account of a decrease in the impedance in this location.

The device may comprise a member for adjusting the current density flowing between the electrodes, notably a manually actuatable member, and/or a device for automatically regulating the current density. The current density ($A/cm^2$) may be regulated so as to ensure the efficacy of the treatment and/or to limit painful sensations. The regulation of the density of the current may be performed manually by the user, the latter being able to modify the magnitude of the current at will, or else when the warning facility signals to him that this is necessary, or automatically, by virtue of a system for servo-controlling the current density.

The device may comprise a system for servo-controlling the current density between the electrodes to the impedance measurement performed by the controlling system.

The warning facility may comprise one at least of an indicator light, of an audio warning facility, and of a vibratory warning facility, the warning facility preferably being triggered when the impedance measured by the controlling system is located in a predefined impedance range.

In one variant embodiment, the electric current between the electrodes is generated by a low-frequency current generator. In one variant embodiment, the electric current is not generated by a voltage generator.

The device may comprise an electronic timeout system configured to control the amount of composition dispensed and/or the duration of the treatment.

Controlling Member

The device may comprise a member for controlling the dispensation of composition, in particular a push-button (for example an ON/OFF button) or a rotary thumbwheel, and/or a device for regulating the composition flow rate. The controlling member is configured to be actuated manually by the user. The controlling member may be configured to allow the dispensation of a dose of composition, or as a variant a continuous stream of the composition to flow. In one exemplary embodiment, the dispensation of composition continues as long as the control member is engaged, for example as long as the push-button is depressed.

The user may trigger the dispensation of composition when the amount of composition present is insufficient to ensure the efficacy of the treatment. The amount of composition may be regulated manually by the user, the latter modifying the amount of composition dispensed at will, or else when the warning facility signals to him that this is necessary, or automatically, by virtue of a system for servo-controlling the amount of composition dispensed to a measurement performed on the keratin materials.

The device may comprise a system for servo-controlling the amount of composition exiting the reservoir to the impedance measurement performed by the controlling system. Servo-control of the dispensation of composition to the impedance of the skin makes it possible to ensure the presence of a sufficient amount of cosmetic composition throughout the treatment. The amount of composition may be regulated automatically, depending on the performed measurement.

The device may comprise a switch allowing the device to be placed in automatic mode, in which the amount of composition dispensed is servo-controlled to the impedance measurement by the controlling system, or in semi-automatic mode, in which the warning facility informs the user if there is a need to modify the amount of composition dispensed. By "semi-automatic mode", what is meant is that the warning facility may warn the user of the need to manually dispense composition. The expression "automatic mode" must be understood to mean that the dispensation of composition is triggered automatically, as mentioned above, as and when it is needed. In this case, the warning facility may be disabled or as a variant signal to the user that the composition is about to be dispensed.

Reservoir

The unit for dispensing the formulation at the outlet of the reservoir may comprise a pump. Advantageously, the dispensing unit comprises an air pump so as to compress the air between the walls of the reservoir and its housing in the device. The walls of the reservoir are preferably flexible and the walls of the housing are preferably rigid.

More advantageously, the housing is airtight. The reservoir is controllably compressed by the air pump. This creates a certain pressure in the housing to regulate the flow rate of formulation. A unidirectional valve at the end of the reservoir may make it possible to keep the formulation from making contact with air.

The reservoir may have a variable internal volume and comprise at least one wall that is elastically deformable so as to decrease the internal volume, in particular two elastically deformable walls facing each another.

The reservoir may be designed to be removably mounted in the device such that, once the reservoir has been emptied, it may be replaced with another, or removed to be filled if the reservoir has a filling orifice.

Advantageously, the reservoir has an elastically deformable outer wall.

Advantageously, the reservoir is formed in one piece. It is preferably molded in one piece, in particular from the same thermoplastic, for example LDPE, HDPE, a mixture of LDPE and HDPE, PP or a mixture of PE and PP in any proportion. The thickness of the wall of the reservoir is for example comprised between 0.1 and 1 mm, and between 0.3 and 0.8 mm in the second region.

In the rest configuration of the deformable region the total internal volume of the reservoir is advantageously comprised between 1 and 100 $cm^3$ and preferably between 20 and 50 $cm^3$. This volume is optimal for a few uses or repeated treatment extending over a few weeks.

Preferably, the internal volume of the reservoir may diminish by a volume of between 10% and 50% of the internal volume of said reservoir in the rest configuration of the deformable region. This variation in volume has the advantage of being visible and measurable.

The reservoir may be manufactured by injection blow molding or extrusion blow molding.

The reservoir may be removable. The reservoir in particular may be a single-use reservoir. It may or may not be single-dose.

Composition

It is possible to use at least one cosmetic or dermatological composition with the device.

The composition(s) used may take any form, for example the form of an aqueous solution, of an oil, of an emulsion, of a powder or of a gel. The composition(s) used may also be sprayed onto the skin.

When the composition(s) used takes/take the form of a gel, the latter may take on the shape of the electrode to which it is applied, as mentioned above.

The composition(s) may comprise an active principle. Advantageously, the composition is chosen from:
- a face care or body care composition, comprising in particular an active agent chosen from humectant or moisturizing active agents, anti-ageing active agents, for example depigmenting active agents, active agents that act on cutaneous microcirculation or seboregulating active agents,
- a composition for making up the face or body,
- a hair composition, in particular a composition for washing the hair, for hair care or conditioning, for temporary form retention or shaping of the hair, for the temporary, semi-permanent or permanent dyeing of the hair, or for relaxing or permanent-waving, in particular a composition for relaxing, dyeing or bleaching the roots and hair,
- a composition for the scalp, in particular an antidandruff composition, a composition for preventing hair loss or for promoting regrowth of the hair, an anti-seborrheic composition, an anti-inflammatory composition, an anti-irritation or soothing composition, a mark-preventing composition or a composition for stimulating or protecting the scalp.

The device can be used in various cosmetic or dermatological treatments, for example for combating wrinkles, herpes, acne or for redensifying the skin or the hair.

BRIEF DESCRIPTION OF THE DRAWINGS

The present invention will be better understood on reading the following detailed description of non-limiting examples of implementation of the invention and on examining the appended drawings, in which.

DETAILED DESCRIPTION

Figure 1:
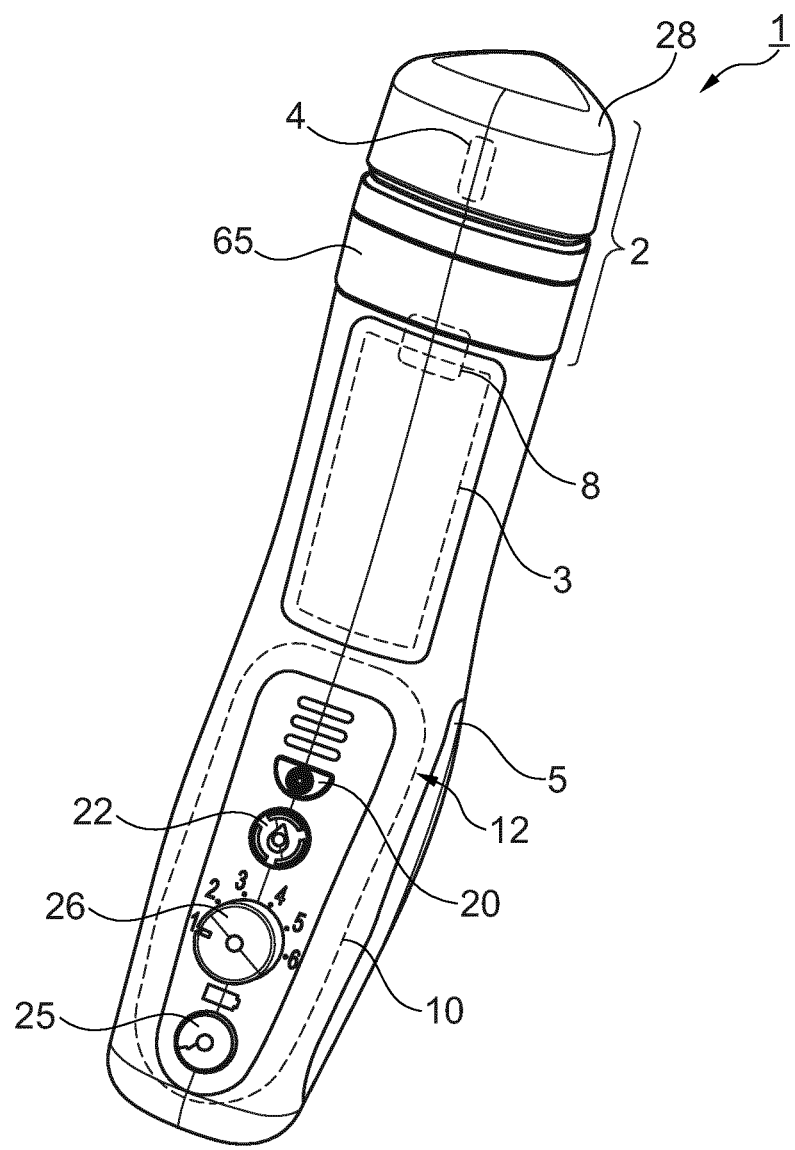
FIG. 1 is a schematic and partial perspective view of a device according to the invention.
Figure 3:
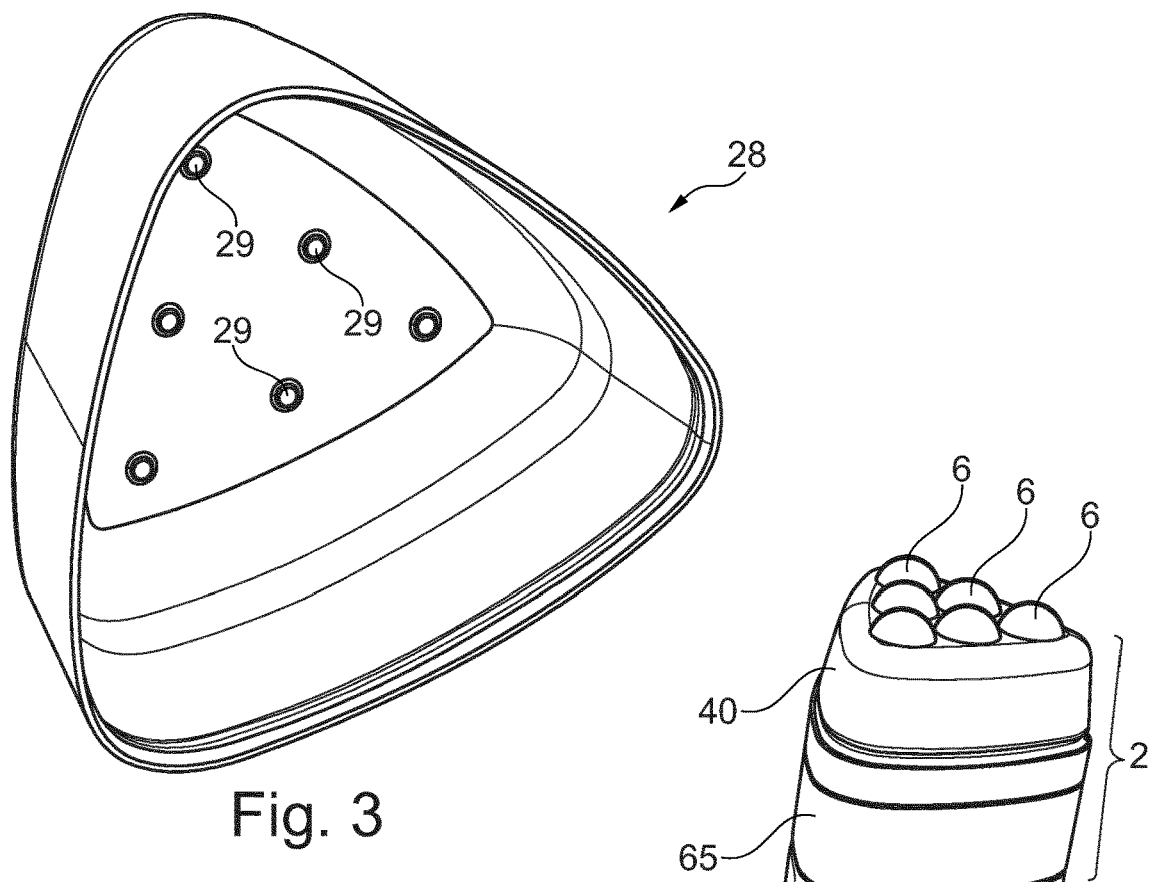
FIG. 3 is a schematic and partial perspective view of the closing cap of the device in FIG. 1, FIGS. 4a and 4b are schematic and partial cross-sectional views of the elastically deformable membrane, in the first position then in the second position, respectively.
Figure 2:
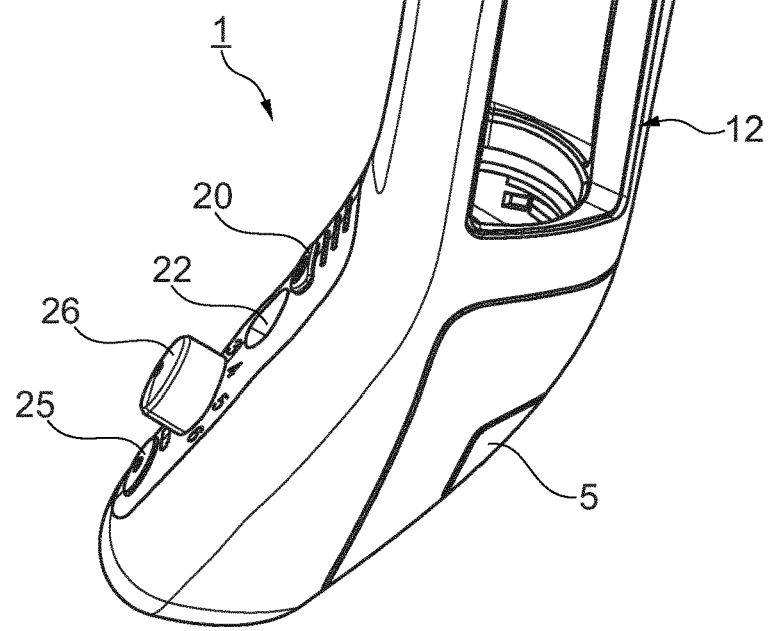
FIG. 2 is a schematic and partial perspective view of a device according to the invention.

FIGS. 1 to 3 show a device 1 according to the invention. It comprises a body 12 on which is mounted an end fitting 2 including six applying members 6 each having a ball shape, and a composition reservoir 3 housed inside the body 12 and shown by a dashed line. The end fitting 2 is fastened by snap-fastening to the body 12. It could be mounted in another way. In the example in question, the body 12 is made of thermoplastic. As a variant, it may be made of any other material. Furthermore, the applying members 6 are plastic balls. The applying members 6 could have any other shape, for example that of rollers.

The applying members 6, which are six in number in the described example, are placed in a triangle, thereby allowing application and treatment of zones that are difficult to access, for example the wings of the nose, to be promoted.

The device 1 includes an electrode 4 (shown by a dashed line in FIG. 1), the electrode 4 being housed inside the end fitting 2, and a counter electrode 5 placed on the body 12. The counter electrode 5 makes contact with the hand of the user when the latter holds the device 1 in his hand, such that the electrical circuit between the electrode 4 and the counter electrode 5 is closed, the current then passing through the body of the user during the treatment. The bias of the electrode 4 and that of the counter electrode 5 may be reversible (+ or −), depending on the nature of the composition used.

Figure 4A:
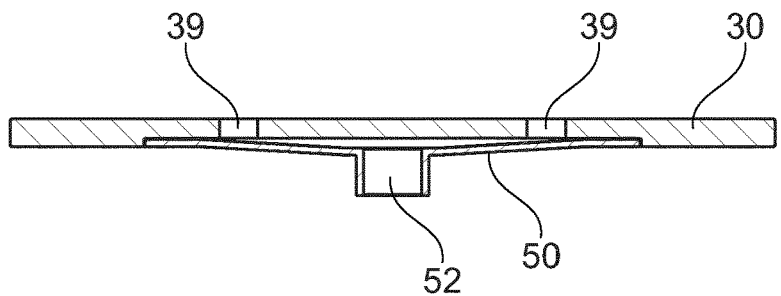
Figure 4B:
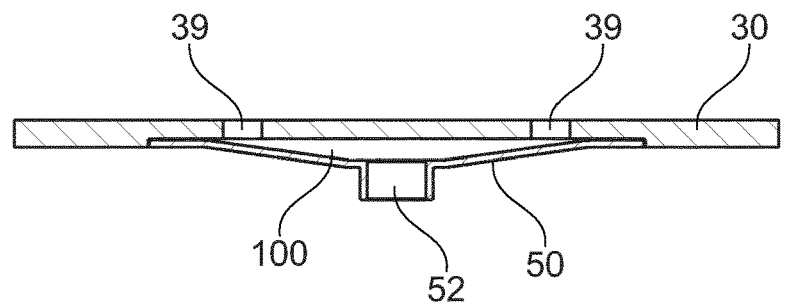

The electrode 4 is connected to a pole of an electrical supply system 10 housed in the body 12 and communicates with the composition when the latter passes into a distributor 30, which is placed under the applying members 6 and illustrated in FIGS. 4a and 4b. The composition thereafter passes over the applying members 6 to arrive at the application surface, the skin in the example described, with a view to treatment. The counter electrode 5 is connected to the other pole of the electrical supply system 10, which is powered by a battery (cell stacks or rechargeable battery).

To begin the treatment, the user turns on the device by means of a push-button 25. When the apparatus is applied, for example to the person's face, an electric current then begins to flow between the electrode 4 and the counter electrode 5 and at the same time the composition contained in the reservoir is dispensed by a dispensing unit 8, in particular a pump, either automatically or by action of the user on a controlling member 22.

In a variant embodiment, the intensity of the current may be adjusted by the user by virtue of an adjustment member 26 for adjusting the current density between the electrodes, which is a graduated rotary button in the example of FIG. 1.

If there is not enough cosmetic composition between the electrode 4 and the skin, the impedance of the skin increases. The device comprises a controlling system that is sensitive to the impedance of the skin and configured to detect such an impedance variation. The device also comprises a warning facility 20 allowing the user to be provided with a signal depending on information originating from the controlling system. In the described example, the warning facility 20 provides a luminous signal. The user may then dispense an additional dose of composition by pressing the member 22 for controlling the dispensation of composition, which is a push-button in the example in FIG. 1.

The structure of the end fitting 2 will now be described in greater detail with reference to FIGS. 2 to 4b.

The end fitting firstly comprises a closing cap 28 (illustrated in isolation in FIG. 3) which is configured to be fastened by snap-fastening to the rest of the device and more particularly to a cover 40 of the applying members 6. The closing cap 28 comprises, in the bottom thereof, dimples 29 for holding the applying members 6 still. This closing cap is preferably not electrically conducting.

The cover 40 allows the applying members 6 to be held in place on a distributor 30. The cover 40 comprises openings through which the applying members 6 protrude toward the exterior in order to allow the composition to be applied. The cover 40 is extended by a top ring 65 of the body 12.

The end fitting comprises an intermediate chamber 100 for storing the composition, which is at least partially defined by an elastically deformable wall. The wall of this intermediate chamber is defined by the distributor 30 and an elastically deformable membrane 50.

The elastically deformable membrane 50 (illustrated in FIGS. 4*a* and 4*b*) is disk-shaped. It includes a channel 52 for conveying the composition into the intermediate chamber. This channel 52 may allow the composition to be conducted from the reservoir to the intermediate chamber.

The distributor 30 bounding the intermediate chamber includes supplying orifices 39 for conducting the composition from the intermediate chamber to the applying members.

The maximum volume of the intermediate chamber 100 is for example about 20 μL. A height h of the intermediate chamber 100 extends between the extreme positions of the elastically deformable membrane 50.

When a certain amount of composition has been dispensed by the dispensing unit from the reservoir, said amount moves through the device to reach the intermediate chamber 100 in which it may be stored before being dispensed onto the keratin materials via the applying members. Under the pressure of the composition, the elastically deformable membrane moves toward said second position, allowing surplus composition to be stored. The application of composition via the applying members may then continue with use of the surplus of composition stored in the intermediate chamber, even if the composition is dispensed by the dispensing unit from the reservoir in fits and starts. Thus, the distribution of the composition onto the keratin materials is smoothed.

In the example just described, the applying members 6 were arranged in a triangle, but they could have been arranged differently.

Figure 5:
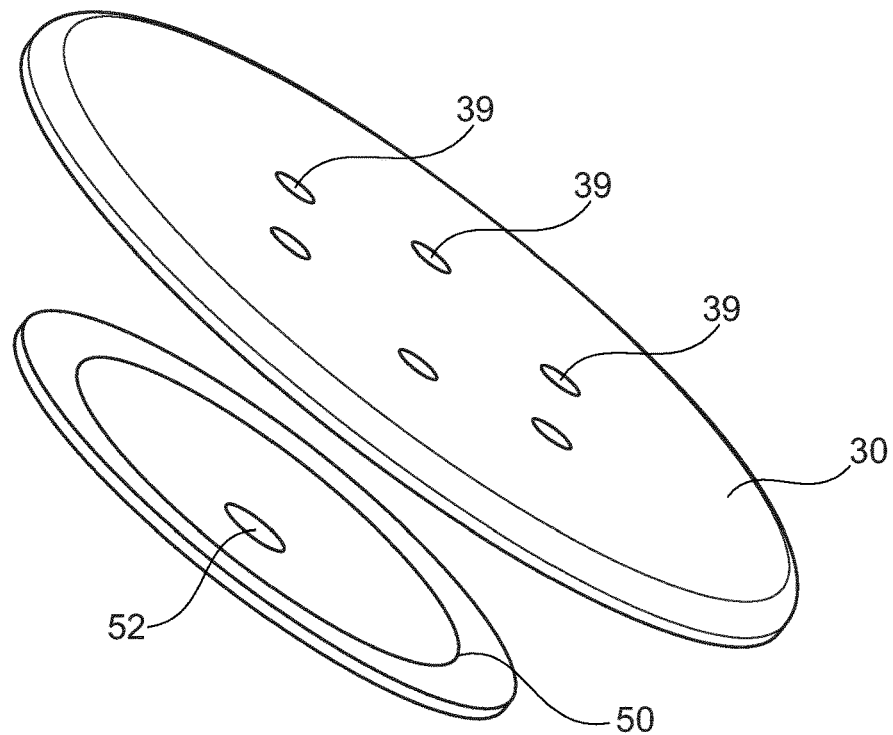
FIG. 5 is a schematic and partial perspective view of a variant embodiment.

In the exemplary embodiment illustrated in FIG. 5, the distributor 30 comprises supplying orifices 39 placed in a hexagon, the applying members 6 also being intended to be placed in a hexagon.

The invention claimed is:

1. A device for treating human keratin materials, with aid of an electric current, comprising:
   a reservoir containing a composition to be applied to the keratin materials,
   a dispensing unit for dispensing the composition contained in the reservoir,
   an end fitting for applying the composition contained in the reservoir, the end fitting being mounted on a body of the device, the end fitting comprising at least one applying member, the applying member being supplied with composition from the reservoir by the dispensing unit, the composition passing through an intermediate chamber for storing the composition located in the end fitting, the intermediate chamber being at least partially defined by an elastically deformable wall, the intermediate chamber being situated in the end fitting between the dispensing unit and the at least one applying member, and
   an electrical supply system for exposing the keratin materials to an electrical treatment current in a zone of application of the composition.

2. The device as claimed in claim 1, wherein the elastically deformable wall of the intermediate chamber comprises an elastically deformable membrane.

3. The device as claimed in claim 2, wherein the elastically deformable membrane is disk-shaped.

4. The device as claimed in claim 1, wherein the elastically deformable membrane comprises a channel for conveying the composition to the intermediate chamber.

5. The device as claimed in claim 1, further comprising a distributor bounding the intermediate chamber and comprising supplying orifices for conducting the composition from the intermediate chamber as far as the applying members, the size of the supplying orifices being chosen such that the elastically deformable wall deforms under the pressure of the composition.

6. The device as claimed in claim 1, comprising a plurality of applying members.

7. The device as claimed in claim 1, wherein at least one applying member is a ball.

8. The device as claimed in claim 1, wherein the maximum volume of the intermediate chamber is comprised between 5 and 100 microliters.

9. The device as claimed in claim 1, wherein the dispensing unit is configured to dispense the composition in fits and starts.

10. The device as claimed in claim 1, wherein the dispensing unit is actuated manually.

11. The device as claimed in claim 1, wherein the dispensing unit is actuated automatically.

12. The device as claimed in claim 11, wherein the dispensing unit includes at least one motor.

13. The device as claimed in claim 1, configured to allow the composition to be dispensed onto the keratin materials with a flow rate comprised between 0.5 and 20 μL/s.

* * * * *